United States Patent [19]
Dolhyj et al.

[11] 3,956,377
[45] May 11, 1976

[54] PRODUCTION OF UNSATURATED ACIDS FROM THE CORRESPONDING ALDEHYDES

[75] Inventors: Serge R. Dolhyj, Parma; Ernest C. Milberger, Solon, both of Ohio

[73] Assignee: The Standard Oil Company (Ohio), Cleveland, Ohio

[22] Filed: June 17, 1974

[21] Appl. No.: 479,724

[52] U.S. Cl. ............................ 260/530 N; 252/462; 252/467; 252/468; 252/469; 252/470
[51] Int. Cl.$^2$ ........................................ C07C 51/26
[58] Field of Search .................... 260/530 N, 533 N

[56] References Cited
UNITED STATES PATENTS 3,642,930  2/1972  Grasselli et al. ................ 260/533 N
3,773,692  11/1973  Hensel et al. .................... 260/530 N
3,775,474  11/1973  Ohara et al. ..................... 260/530 N

*Primary Examiner*—James A. Patten
*Assistant Examiner*—Michael Shippen
*Attorney, Agent, or Firm*—Herbert D. Knudsen

[57]  ABSTRACT

Coated catalysts having an inert support material with an outer surface and a coating of active catalyst containing tungsten, vanadium and molybdenum plus optionally one or more of Fe, Mn, Cu, Sn, Sb, Cr, Ce, U, Co, Ni, Zn, Mg or mixture thereof have been found to be especially effective catalysts for the production of unsaturated acids from the corresponding unsaturated aldehydes, for example, acrolein is oxidized to acrylic acid using these catalysts. The catalysts give a very low exotherm, very high single pass yields of the desired acid and reduce the undesirable by-products.

9 Claims, No Drawings

PRODUCTION OF UNSATURATED ACIDS FROM THE CORRESPONDING ALDEHYDES

BACKGROUND OF THE INVENTION

The active catalytic materials of the present invention are known and the preparations are known. For example, the base catalyst of the invention employing tungsten, vanadium and molybdenum is shown in U.S. Pat. No. 3,567,773. Other catalysts of the invention are known in the art and the present invention does not modify these active catalysts. These catalysts of the art have been shown to be especially effective for the production of acrylic acid and methacrylic acid from the corresponding aldehyde. It is the aim of the present invention to make these catalysts even more effective for the production of unsaturated acids.

SUMMARY OF THE INVENTION

It has been discovered in the process for the preparation of acrylic acid or methacrylic acid by the oxidation of acrolein or methacrolein in the presence of an active catalyst of the formula $$A_a W_b V_c Mo_d O_x$$

wherein
A is Fe, Mn, Cu, Sn, Sb, Cr, Ce, U, Co, Ni, Zn, Mg or mixture thereof; and
wherein
a is 0–12;
b is about 0.1 to about 16;
c is about 0.5 to about 12;
d is about 8 to about 16; and
x is the number of oxygens required to satisfy the valence requirements of the other elements present.

At an elevated temperature of about 200° to about 500°C, the improvement comprising
using a coated catalyst consisting essentially of an inert support material having a diameter of at least 20 microns and an outer surface and a continuous coating of said active catalyst on said inert support strongly adhering to the outer surface of said support.

By use of these coated catalysts in the reaction to produce unsaturated acids, a very low exotherm is realized allowing for better control of the reaction. High single pass yields are exhibited and the elimination of undesirable by-products is obtained.

The central aspect of the present invention is the special coated catalyst employed. The special coated catalyst consists of an inner-support material having an outside surface and a coating of the active catalytic material on this outside surface. These catalysts can be prepared by a number of different methods.

The support material for the catalyst forms the inner core of the catalyst. This is an essentially inert support and may have substantially any particle size although a diameter of greater than 20 microns is preferred. Especially preferred in the present invention for use in a commercial reactor are those supports which are spherical and which have a diameter of about ⅛ to about ½ inches. These inert support materials may be selected from a wide variety of materials which are known to be substantially inert in the oxidation reaction. By the term "substantially inert" is meant those materials which provide a per pass conversion of less than about 20 percent in the production of acrylic acid from acrolein under the reaction conditions. Suitable materials for these supports are normally oxides with silica, alumina, alumina-silica, silicon carbide, titania and zirconia being preferred.

The second component of the coated catalyst is the active catalytic material which is coated on the inert support. These active catalytic materials may be any of the materials that fit the formula described above. As discussed previously in the background of the invention, these catalytically active materials are well known but their use in coated catalysts is not known. Preferred active catalytic materials are those described by the formula above that contain tungsten, vanadium and molybdenum alone, i.e. where A is zero. Also preferred are those catalysts wherein a is greater than zero and A is Ce, Cu, U, Co, Sn, Sb, Cr or mixture thereof. Specific catalysts of special interest are those that contain tin or copper alone or in combination with other materials such as antimony or chromium.

The coated catalysts are prepared from these active catalytic materials and a support material. The most convenient method of accomplishing this partially wetting the support material with water and rolling the partially wet support material in a powder of the active catalyst. This is suitably accomplished by placing the partially wet suppport material in a rotating drum or jar and adding powdered catalyst to the rotating material. A uniformly coated catalyst is obtained.

The process for the oxidation of acrolein to acrylic acid or the oxidation of methacrolein or methacrylic acid is well known in the art. Broadly, these reactions are carried out by contacting a mixture of the unsaturated aldehyde and molecular oxygen with the catalyst at an elevated temperature of about 200° to about 500°C. These reactions can be conducted at atmospheric, superatmospheric or subatmospheric pressure using contact times of less than a second to a few seconds or more. The reaction is most suitably conducted in a fixed-bed reactor, although the reaction can also be conducted in a fluid-bed reactor provided that the support material is small enough in terms of particle size.

The three basic advantages of the present invention are 1) that the exotherm of the reaction is substantially lower, in other words the difference between the bath temperature and the reaction temperature is very much smaller than use of the pure catalytic material alone or even the catalytic material mixed with a support material; 2) it has been found that the per pass conversion obtained using the coated catalyst is as good or better than the uncoated catalysts; 3) it has been found that the coated catalysts in some cases essentially eliminate the formation of the undesirable by-product acetic acid. With these advantages, the catalyst of the invention used in the production of unsaturated acids provides a very substantial advance in this commercial technology.

SPECIFIC EMBODIMENTS

Comparative Examples A-B and Examples 1–2

Comparison of Coated Catalysts to Uncoated Catalysts

A base catalyst of the invention containing $W_{1.2}V_3Mo_{12}O_x$ was prepared from 72.0 g. $MoO_3$, 11.3 g. $V_2O_5$ and 9.19 g. tungsten metal powder by reflux in water. The resulting slurry was evaporated and dried at about 115°C for the three days. A dry powder was obtained. This powder was coated on 10/30 mesh SA 5223 Alundum by taking 25 g. of Alundum, setting the Alundum with 1.03 cc. of water and adding 6.25 g. of active catalyst prepared above in five equal portions. During and after each addition, the Alundum was rolled in a glass jar. Hard uniform coated catalysts were obtained that consisted of the Alundum support with a continuous, strongly adhering coat of the active catalyst.

The oxidation experiments were run in a 20 cc. tubular reactor constructed of a 1 cm. inside diameter stainless steel tube. Acrolein/air/steam were fed as the reactants in a ratio of 1/10/6. The results are shown in Table I and are stated as follows:

Comparative Examples C and D and Examples 3–7

Effect of Various Levels of Active Catalyst

In the same manner as shown above, an active catalyst of $Cu_2Sn_{0.5}W_{1.2}V_3Mo_{12}O_x$ was prepared and coated on Alundum at different levels. The results of these experiments are shown in Table II. The production of acrylic acid from acrolein was carried out as above.

Table II

Effect of Various Levels of Active Catalytic Material in the Reaction of Acrolein to Obtain Acrylic Acid

| Example | Catalyst | Temperatures, °C Bath | Exotherm | ΔT | Contact Time, Sec. | Single Pass Yield Acrylic Acid | Acetic Acid | Results, % Conversion | Selectivity |
|---|---|---|---|---|---|---|---|---|---|
| Comp. C | Uncoated | 218 | 227 | 8 | 2.4 | 94.8 | 0 | 95.8 | 98.9 |
| Comp. D | Uncoated | 232 | 261 | 29 | 2.2 | 96.5 | 0.5 | 100 | 96.5 |
| 3 | Coated 20% Active | 246 | 251 | 6 | 2.2 | 92.8 | 0 | 94.5 | 98.2 |
| 4 | Coated 20% Active | 260. | 268 | 8 | 2.1 | 98.2 | 0 | 100 | 98.2 |
| 5 | Coated 30% Active | 232 | 239 | 7 | 2.3 | 91.4 | 0 | 93.0 | 98.3 |
| 6 | Coated 30% Active | 246 | 254 | 8 | 2.2 | 98.2 | 0 | 100 | 98.2 |
| 7 | Coated 40% Active | 232 | 242 | 10 | 2.2 | 97.7 | 0 | 100 | 97.7 |

Comparative Examples E and F and Examples 8–10

Cerium-Containing Catalysts

In the same manner as described above cerium catalysts of the formula $Ce_3W_{1.2}V_3Mo_{12}O_x$ were prepared and tested in the production of acrylic acid. The results are shown in Table III.

Table III

Effect of Coating on Cerium-Containing Catalysts

| Example | Catalyst | Bath | Exotherm | ΔT | Contact Time, Sec. | Single Pass Yield* | Results, % Conversion | Selectivity |
|---|---|---|---|---|---|---|---|---|
| Comp. B | Uncoated | 288 | 301 | 13 | 2.0 | 96.1 | 100 | 96.1 |
| 8 | Coated 30% Active | 288 | 294 | 7 | 2.0 | 73.7 | 75.7 | 97.3 |
| 9 | Coated 30% Active | 316 | 321 | 6 | 1.9 | 87.7 | 91.0 | 96.3 |
| 10 | Coated 30% Active | 329 | 335 | 6 | 1.9 | 96.0 | 100 | 96.0 |

*no acetic acid was formed in any of the experiments $$\% \text{ single pass yield} = \frac{\text{moles of product produced} \times 100}{\text{moles of acrolein fed}}$$

$$\% \text{ conversion} = \frac{\text{moles of acrolein reacted} \times 100}{\text{moles of acrolein fed}}$$

$$\% \text{ selectivity} = \frac{\text{moles of acrylic acid produced} \times 100}{\text{moles of acrolein reacted}}$$

Table I

Effect of Coating on Performance of Catalyst of $W_{1.2}V_3Mo_{12}O_x$

| Example | Catalyst | Temperatures, °C Bath | Exotherm | ΔT | Contact Time, Sec. | Single Pass Yield Acrylic Acid | Acetic Acid | Results, % Conversion | Selectivity |
|---|---|---|---|---|---|---|---|---|---|
| Comp. A | Uncoated | 232 | 256 | 23 | 2.2 | 90.2 | trace | 100 | 90.2 |
| Comp. B | Uncoated | 260 | 294 | 34 | 2.1 | 84.1 | 2.3 | 100 | 84.1 |
| 1 | Coated | 260 | 269 | 9 | 2.1 | 87.7 | 0 | 93.6 | 93.7 |
| 2 | Coated | 274 | 282 | 8 | 2.0 | 92.7 | 0 | 99.6 | 93.1 |

It is seen from the data above that the catalysts of the invention are superior in that they exhibit lower exotherms, produce higher single pass yields of acrylic acid and no acetic acid by-product.

We claim:
1. In the process for the preparation of acrylic acid or methacrylic acid by the oxidation of acrolein or methacrolein in the presence of an oxide or oxide complex active catalyst of the formula

$$A_a \ W_b \ V_c \ Mo_d \ O_x$$

wherein
A is Fe, Mn, Cu, Sn, Sb, Cr, Ce, U, Co, Ni, Zn, Mg or mixture thereof; and
wherein
$a$ is 0–12;

$b$ is about 0.1 to about 16;
$c$ is about 0.5 to about 12;
$d$ is about 8 to about 16;
$x$ is the number of oxygens required to satisfy the valence requirements of the other elements present, at an elevated temperature of about 200° to about 500°C., the improvement comprising using a coated catalyst consisting essentially of an inert support material having a diameter of at least 20 microns and an outer surface and a continuous coating of said active catalyst on said inert support strongly adhering to the outer surface of said support, said coated catalyst being prepared by partially wetting the support with water and rolling the partially wet support in a powder of the active catalyst.

2. The process of claim 1 wherein the active catalyst is about 10 to about 100 percent by weight of the inert support.

3. The process of claim 1 wherein the inert support is selected from the group consisting of silica, alumina, alumina-silica, silicon carbide, titania and zirconia.

4. The process of claim 1 wherein $a$ of the formula of the active catalyst is zero.

5. The process of claim 1 wherein $a$ of the formula of the active catalyst is greater than zero and A is Ce, Cu, U, Co, Sn, Sb, Cr or mixture thereof.

6. The process of claim 5 wherein A is Sn, Cu or mixture thereof.

7. The process of claim 5 wherein A is Cu.

8. The process of claim 5 wherein A is Sb and Cu.

9. The process of claim 5 wherein A is Cr and Cu.

* * * * *